United States Patent
Kubitzek

(10) Patent No.: US 7,023,555 B2
(45) Date of Patent: Apr. 4, 2006

(54) MEASURING APPARATUS

(75) Inventor: Rüdiger Kubitzek, Geilenkirchen (DE)

(73) Assignee: STEAG ETA-Optik GmbH, (DE)

( * ) Notice: Subject to any disclaimer, the term of this patent is extended or adjusted under 35 U.S.C. 154(b) by 343 days.

(21) Appl. No.: 10/466,582

(22) PCT Filed: Jan. 15, 2002

(86) PCT No.: PCT/EP02/00322

§ 371 (c)(1),
(2), (4) Date: Jul. 18, 2003

(87) PCT Pub. No.: WO02/057755

PCT Pub. Date: Jul. 25, 2002

(65) Prior Publication Data

US 2004/0051874 A1    Mar. 18, 2004

(30) Foreign Application Priority Data

Jan. 19, 2001  (DE) .............................. 101 03 163

(51) Int. Cl.
*G01N 21/55*    (2006.01)
*G01J 3/46*     (2006.01)

(52) U.S. Cl. ...................................... 356/445; 356/402

(58) Field of Classification Search ................ 356/445, 356/402
See application file for complete search history.

(56) References Cited

U.S. PATENT DOCUMENTS

| 5,196,906 | A | * | 3/1993 | Stover et al. | ............... 356/446 |
| 5,754,283 | A | * | 5/1998 | Keane et al. | ............... 356/402 |
| 6,097,025 | A |   | 8/2000 | Modlin et al. | |
| 6,631,000 | B1 | * | 10/2003 | Schwarz | ..................... 356/445 |

FOREIGN PATENT DOCUMENTS

| DE | 31 45 633 | 8/1983 |
| WO | WO 96/13709 | 5/1996 |

OTHER PUBLICATIONS

JP 0 7218344, Patent Abstracts of Japan.

* cited by examiner

*Primary Examiner*—F. L. Evans
*Assistant Examiner*—Kara Geisel
(74) *Attorney, Agent, or Firm*—Robert W Becker & Associates; Robert W Becker

(57) ABSTRACT

A measuring apparatus for measuring color characteristics of an object is provided. The apparatus includes at least two measuring units, each of which has at least one optical emitter and at least one optical receiver, wherein the measuring units are combined to form a measuring arrangement. The emitter has an illuminating angle and the receiver has a receiving angle, wherein relative to the object these angles are different for each measuring unit. Respective light guide terminals are provided for each measuring unit. A light source is connectable in common for at least two measuring units via a light guide and a light guide terminal. A detector is connectable in common for at least two measuring units via another light guide and light guide terminal. The light guide terminals can be selectively coupled with the light source and the detector.

14 Claims, 2 Drawing Sheets

MEASURING APPARATUS

BACKGROUND OF THE INVENTION

The invention relates to a measuring apparatus having at least one measuring unit, which in turn is provided with at least one optical emitter and at least one optical receiver, and at least one light source, which is connected with the measuring unit via a light guide, as well as a detector that is connected with the measuring unit via a light guide.

Known color-measuring systems have a single fixed emitter and receiver arrangement. In this connection, conventionally only one light source and only one detector are used. The illumination is frequently effected with halogen light sources or xenon light sources in a pulse or continuous mode operation. The light source illuminates the sample to be measured directly, although it is generally coupled to a light guide. The light guide then illuminates the probe either directly via a round fiber bundle, an annular light arrangement of fibers, or a plurality of fiber bundles that illuminate the sample to be measured from different directions. It is furthermore known to columnate or parallelize the light exiting the light guide via an optical emitter in order to achieve a defined direction of illumination. As detectors, often either three photocells having appropriate optical filters are utilized pursuant to the three-region method, or a three-element photocell having vapor-coated optical filters is used. It is furthermore known to use spectral photometers having a rotary grid, or to use diode line-scanning or CCD line-scanning spectrometers having a fixed grid. The coupling of the detector is generally effected via a light guide. In this connection, an optical measuring head for parallelization, that is also designated as a receiving measuring head, could be disposed between the sample to be measured and the light guide. With the known arrangements, only one fixed illumination and receiving geometry is utilized for the color measurement at the sample.

Furthermore known are measuring apparatus for color-measuring systems that, at a number of angles, measure characteristics, in particular the color of an object that is to be measured. With one type of the known measuring systems, the measurement is effected either with a fixed illumination angle and a plurality of fixed receiving angles, or with a fixed receiving angle and a plurality of fixed illumination angles. Measuring systems of this type of construction are particularly unsuitable for use when measuring the angle-dependent color characteristics of novel lacquers and colors. For an adequate characterization of the colors, neither a single illumination angle nor a single receiving angle can be fixedly prescribed. This generally means that a plurality of detector units, such as, for example, spectrometers, and possibly also a plurality of illumination units, must be utilized, which leads to higher costs due to the increased expenditure for components. Furthermore, all of the measuring geometries must be simultaneously disposed over the sample, as a result of which the geometric possibilities for the arrangement of the measuring heads is limited, and not all desired illumination angles and receiving angles can be measured.

With a second known type of measuring system, the illumination angle and the receiving angle can be adjusted manually or in a motorized manner. Such a goniometer offers the possibility of setting any desired illumination angle by two movable measuring heads.

However, goniometers are difficult to adjust and, due to the susceptibility to adjustment, they can be used only or laboratory purposes, but not for routine production controls. Furthermore, the expenditure for apparatus for automated goniometers having motor control is high, as a result of which the apparatus are expensive. Furthermore, generally light sources and detectors are coupled to the measuring heads via light guides, so that a movement of the measuring heads leads to an alteration in the bending curves of the light guides and changes in the spectral transmission of the optical fibers occurs. Therefore, imprecise measurements result with goniometers due to a movement of the measuring heads relative to the light source and the detector, which have a disadvantageous effect upon the precision of the color value determination.

Due to the increasing use of lacquers and colors having angle-dependent color characteristics, i.e. a color characteristic that is a function of the illumination angle as well as of the viewing or receiving angle, the demand for precise multiple-angle color measuring apparatus is increasing.

It is therefore an object of the invention to provide a measuring apparatus with which the above-mentioned drawbacks of conventional measuring systems are avoided, and in particular to enable a determination that is as precise as possible of the color characteristics as a function of the angle and to accomplish this at different illumination and receiving geometries.

SUMMARY OF THE INVENTION

The stated object is realized pursuant to the inventive measuring apparatus in that at least two measuring units are combined to form a measuring arrangement, the measuring units each have light guide terminals, and these terminals can be selectively coupled with a light source, which is connectable in common for at least two measuring units, or with a detector, which is connectable in common for at least two measuring units.

It is advantageous if the illumination and receiving angle of the emitter and receiver of a measuring unit are different relative to an object to be measured for each measuring unit, in order to realize different illumination and receiving angles for the color measurement in one and the same measuring apparatus.

A further advantage of the present invention is that each emitter and each receiver of a measuring unit is respectively connected via an emitter or receiver light guide with the respective terminal of the measuring unit, and these light guides are advantageously rigidly disposed in the measuring unit. Thus, when the entire measuring unit moves, there is no change of the bending curves of the light guides, which otherwise could lead to changes in the spectral transmissions of the optical light guides and have a disadvantageous effect upon the precision of the color value determinations.

Pursuant to a further very advantageous embodiment of the invention, the light source and detector light guides are coupled with the respective terminal of a measuring unit in a contact-free manner. By shifting the measuring units, a coupling between the light source and detector light guides on the one hand, and light guides of different measuring units on the other hand, is made possible, which is designated as fiber multiplexing.

It is advantageous to provide an optical coupling device between the light source and detector light guides on the one hand, and the terminal of the measuring unit on the other hand. This enables a precise and reliable coupling between the light guides.

A further very advantageous embodiment of the invention results if the measuring arrangement is movable relative to the object that is to be measured. By moving the measuring units that are combined in the measuring arrangement, any desired measuring unit can be moved to the sample. This is designated as measuring head multiplexing.

Pursuant to a further advantageous embodiment of the invention, the movement of the measuring arrangement is linear or alternatively is a rotational movement.

During movement of the measuring arrangement, the light source and detector light guides are preferably coupled with respective terminals of different measuring units to ensure the aforementioned fiber multiplexing.

Pursuant to one embodiment of the invention, the respective measuring unit is disposed at the same location relative to the object being measured during the measuring process. This ensures that merely specific illumination angles and receiving angles of the measuring unit are the only variable measuring parameter.

Pursuant to a further advantageous embodiment of the invention, the measuring units of the measuring arrangement are disposed in a circular manner, which enables a movement of the measuring units via a rotational movement.

Pursuant to a further embodiment of the invention, the measuring units of the measuring arrangement are disposed linearly in order to shift the measuring units by a linear, transverse movement.

A further very advantageous embodiment of the invention exists if a plurality of light sources can be coupled with the measuring units via respective light guides, thereby achieving a greater flexibility during the construction.

Pursuant to a further embodiment, a plurality of detectors are advantageously coupled with the measuring units via respective light guides in order to simultaneously read different measuring parameters of several measuring units and/or different measuring units.

BRIEF DESCRIPTION OF THE DRAWINGS

The invention, as well as further embodiments and advantages, will be explained subsequently with reference to the figures.

DESCRIPTION OF PREFERRED EMBODIMENTS

Figure 1:
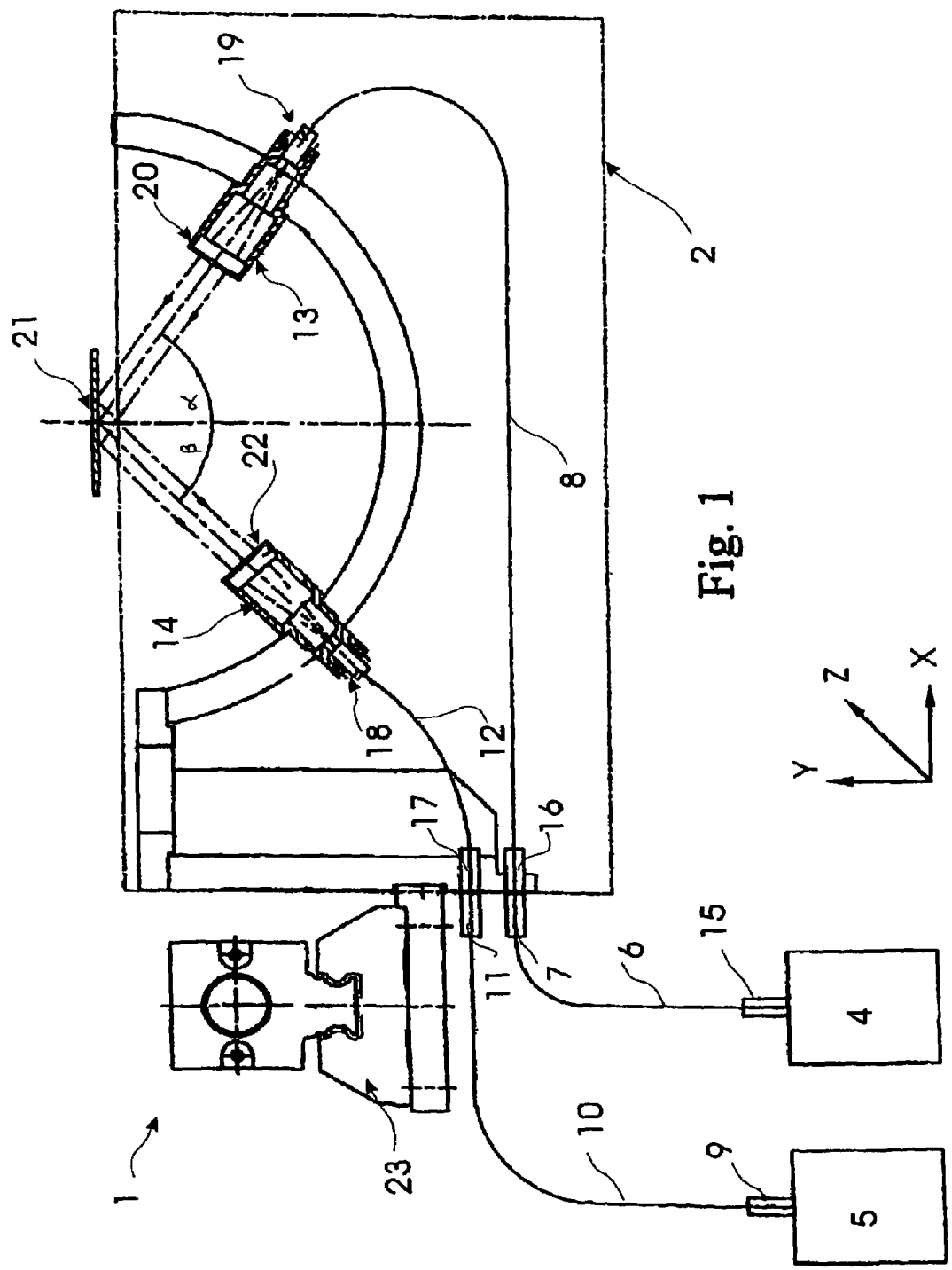
FIG. 1 a schematic view of one embodiment of the inventive measuring apparatus.

Referring to FIG. 1, a measuring apparatus 1 for the angle-dependent measurement of color characteristics of lacquers and colors is described. The measuring apparatus 1 has a plurality of measuring units 2, which are combined to form a measuring arrangement 3 (see FIGS. 2 and 3). The measuring apparatus 1 is furthermore provided with a light source 4 and a detector 5. In the preferred embodiment, the light source 4 is a halogen light source 4 that couples light in one end 15 of a light guide 6. The light guide 6 serves as an illuminating fiber, and at its other end 7 can be coupled with a light guide 8 of a measuring unit 2. In the preferred embodiment, the detector 5 is a diode line-scanning spectrometer. The spectrometer 5 is coupled to one end 9 of a light guide 10. The light guide 10 serves as a receiving fiber, and its other end 11, similar to the situation with the light guide 6, is coupled to a light guide 12 of the measuring unit 2.

The measuring unit 2 includes two optical measuring heads, an illuminating measuring head or emitter 13 and a receiving measuring head or receiver 14. The emitter 13 is connected with an emitter light guide 8 at the reference numeral 19, whereby the emitter light guide 8 connects the emitter with light guide terminals 16, 17 of the measuring unit 2. Similarly, the receiver 14 is connected with one end 18 of a receiver light guide 12, whereby the receiver light guide 12 leads to a light guide terminal 17 of the measuring unit. With appropriate positioning of the measuring unit 2, the ends 7,11 of the light source and detector light guides 6,10 are disposed ahead of the corresponding ends 16,17 of the emitter and receiver light guides 8, 12. In this configuration, light from the light source light guide 6 is coupled into the emitter light guide 8, and light from the receiver light guide 12 is coupled into the detector light guide 10. Pursuant to a further embodiment of the invention, instead of a direct coupling of the fiber ends 11, 6 and 12, 10 to one another via a slight spacing, the coupling can also be effected via imaging optics.

With appropriate coupling of the emitter 13 to the light source 4, the light exiting the emitter light guide 8 is parallelized or columnated in the emitter 13 via an optical device 20, and illuminates, at art angle $\alpha$, an to object 21 that is to be measured and that is located in front of the measuring unit 2. A portion of the light deflected back at the object 21 impinges upon the receiver 14 at an angle $\beta$, and is focused by an optical device 22 of the receiver 14 to the end 18 of the receiver light guide 12. With appropriate coupling of the receiver 14 to the detector 5, the light reflected from the object to be measured is guided to the detector 5, where it is spectrally measured. The color values can thus be determined as a function of the illuminating angle $\alpha$ and the receiving angle $\beta$.

Figure 2:
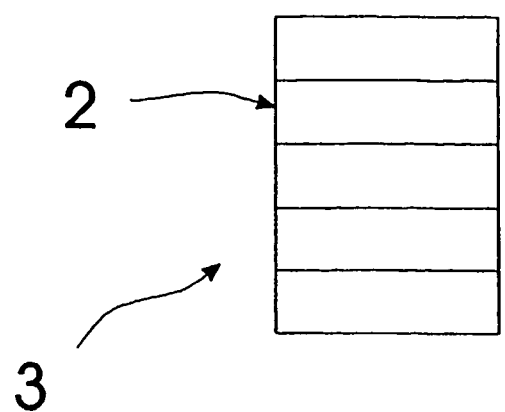
FIG. 2 an embodiment of the arrangement of measuring units in a measuring apparatus FIG. 3 a sketch of a further embodiment of the measuring apparatus.
Figure 3:
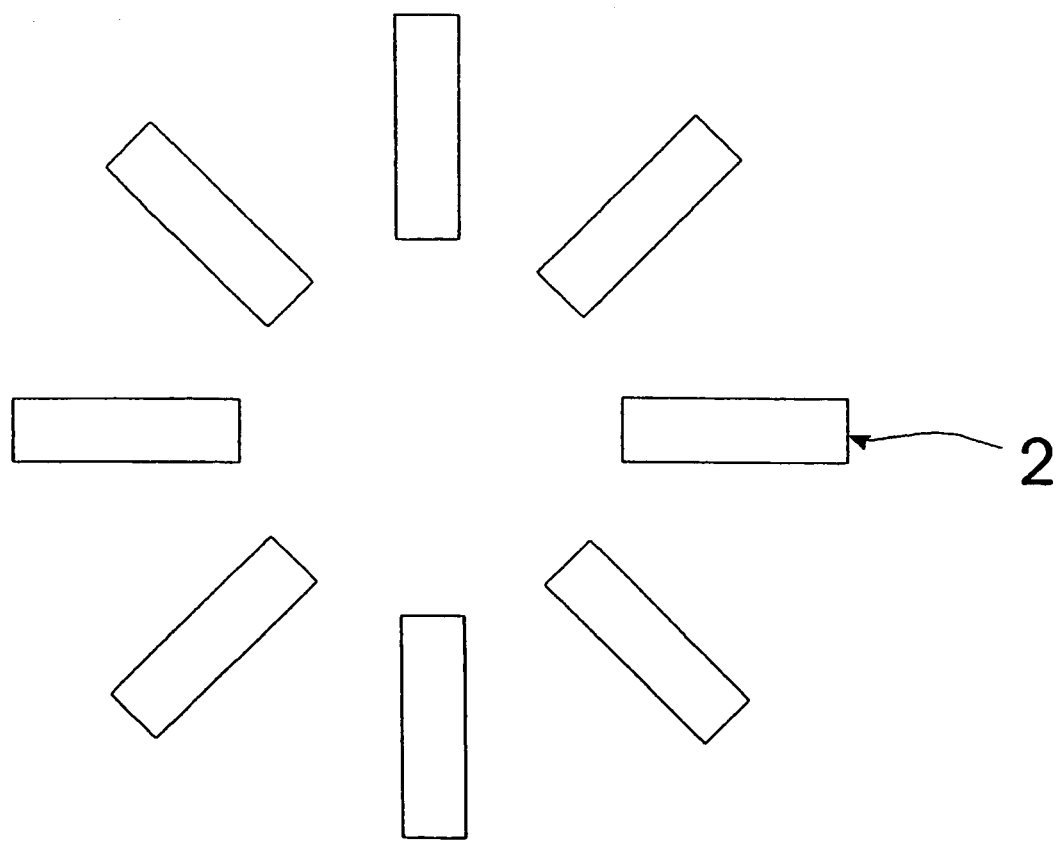

As already mentioned previously, in principle any number of measuring units 2 can be provided. The measuring units 2 that are combined to form the measuring arrangement 3 can, as illustrated in FIG. 2, form a stack. Pursuant to a further embodiment of the present invention, the measuring units 2 are disposed in a ring-shaped manner, as shown in FIG. 3, to form the measuring arrangement 3. In principle, the measuring units 2 have the same construction, although they differ with regard to the illuminating and receiving angles of the emitter 13 and of the receiver 14 relative to the object 21 to be measured for each measuring unit 2. The measuring arrangement 3 is arranged so as to be movable, and can be transversely moved as an entire rigid unit by a linear unit 23 in the z direction (see FIG. 1), i.e. perpendicular to the plane of the drawing sheet. As a result of this transverse movement, any desired measuring unit 2 can be moved below the object 21 to be measured (also known as measuring head multiplexing), whereby due to this displacement, at the same time the free light guide ends 16,17 of the emitter and receiver light guides 8,12 of the measuring unit 2 are coupled to the light source and detector light guides 6,10 (which is designated as filament multiplexing).

Instead of a linear unit for the aforementioned combination of measuring head multiplexing and fiber multiplexing, it is also possible to use a rotary, unit (not shown) that rotates a measuring arrangement 3 such as that shown in FIG. 3. In this connection, however, the maximum number of measuring units 2 is limited by the 360° overall angle of rotation that is available.

The measuring apparatus 1 described above thus offers the possibility to rapidly, and possibly also automatically, switch between different measuring geometries. By means of a displacement of the measuring arrangement 3, different measuring units 2 are coupled with the detector 5 and the light source 4, and are used for the measurement.

In contrast to conventional measuring systems, the components of each measuring unit 2 form a rigid unit. In particular, the emitter and receiver light guides 8, 12 are fixedly mounted within the measuring unit 2. This ensures that during a movement of the measuring arrangement 3, no alteration of the bending curves of the emitter and receiver light guides 12, 8 are produced. The inventive measuring apparatus 1 thus enables a multiple angle color measurement by the use of the individually configured measuring units 2, without thereby causing changes in the bending curves of the light guides by possible changes of the positions thereof. Changes in the spectral transmissions of the light guide 6, 10, 8, 12, which would have a negative impact upon the precision of the color value determination, are thus precluded.

Pursuant to the above preferred embodiment, advantageously merely one light source 4 and one detector 5 can be selectively coupled to all measuring units 2. Pursuant to further embodiments of the invention, however, a plurality of light sources 4 and detectors 5 can preferably be coupled via respective light guides to the measuring units 2 and their respective terminals 16, 17 to provide different types of luminous sources 4, different detectors 5 for measuring a plurality of parameters, and/or for providing redundancy in a measurement.

The specification incorporates by reference the disclosure of German priority document 101 03 163.7 filed Jan. 19, 2001 and PCT/EP02/00322 filed Jan. 15, 2002.

The present invention is, of course, in no way restricted to the specific disclosure of the specification and drawings, but also encompasses any modifications within the scope of the appended claims.

The invention claimed is:

1. A measuring apparatus, for measuring color characteristics of an object that is to be measured, comprising:
    at least two measuring units, each of which has at least one optical emitter and at least one optical receiver, wherein said measuring units are combined to form a measuring arrangement, wherein said optical emitter has an illuminating angle and said optical receiver has a receiving angle, and wherein relative to said object that is to be measured, said illuminating angle and said receiving angle are different for each measuring unit;
    respective first and second light guide terminals for each of said measuring units;
    a light source that via a first light guide and said first light guide terminal is connectable in common for at least two measuring units; and
    a detector that via a second light guide and said second light guide terminal is connectable in common for at least two measuring units, wherein said first and second light guide terminal, are adapted to be selectively coupled with said light source and said detector respectively.

2. A measuring apparatus according to claim 1, wherein a respective emitter light guide and receiver light guide are provided for connecting each optical emitter and each optical receiver of a measuring unit with the respective first and second light guide terminals.

3. A measuring apparatus according to claim 2, wherein said emitter and receiver light guides of a given measuring unit are rigidly disposed therein.

4. A measuring apparatus according to claim 1, wherein at least one of said first and second light guides is coupled in a contact-free manner with the respective first and second light guide terminal of a given measuring unit.

5. A measuring apparatus according to claim 1, wherein an optical coupling device is provided between said first and second light guides on the one hand, and said light guide terminals of a given measuring unit.

6. A measuring apparatus according to claim 1, wherein said measuring arrangement is movable relative to said object that is to be measured.

7. A measuring apparatus according to claim 6, wherein said movement is linear.

8. A measuring apparatus according to claim 6, wherein said movement is a rotational movement.

9. A measuring apparatus according to claim 6, wherein during a movement of said measuring arrangement, said first and second light guides are coupled via respective first and second light guide terminal with different ones of said measuring units.

10. A measuring apparatus according to claim 1, wherein during a measuring process, a respective one of said measuring units is disposed at the same location relative to an object that is to be measured.

11. A measuring apparatus according to claim 1, wherein said measuring units of said measuring arrangement are arranged in a circular manner.

12. A measuring apparatus according to claim 1, wherein said measuring units of said measuring arrangement are arranged in a linear manner.

13. A measuring apparatus according to claim 1, wherein a plurality of light sources are adapted to be coupled with said measuring units via respective light guides.

14. A measuring apparatus according to claim 1, wherein a plurality of detectors are adapted to be coupled with said measuring units via respective light guides.

* * * * *